United States Patent [19]

Singh et al.

[11] Patent Number: 5,488,133
[45] Date of Patent: Jan. 30, 1996

[54] IODINATED AROYLOXY KETONES

[75] Inventors: Baldev Singh, Collegeville; Edward R. Bacon, Audubon; Shaughnessy Robinson, Gilbertsville, all of Pa.

[73] Assignee: Eastman Kodak Company, Rochester, N.Y.

[21] Appl. No.: 209,181

[22] Filed: Mar. 10, 1994

[51] Int. Cl.$^6$ .......................... C07C 229/56; A61K 49/04
[52] U.S. Cl. ..................... 424/9.45; 560/103; 560/106; 560/111; 560/47; 424/9.4; 424/9.44
[58] Field of Search ................................. 424/5; 560/47, 560/103, 106, 111

[56] References Cited

U.S. PATENT DOCUMENTS

| | | | |
|---|---|---|---|
| 3,097,228 | 7/1963 | Larsen | 260/471 |
| 3,144,479 | 8/1964 | Obendorf | 260/471 |
| 4,567,034 | 1/1986 | Charles et al. | 424/5 |
| 4,607,123 | 8/1986 | Schuster et al. | 564/153 |
| 5,260,478 | 11/1993 | Bacon et al. | 560/110 |
| 5,346,688 | 9/1994 | Bacon et al. | 424/5 |
| 5,360,604 | 11/1994 | Ruddy et al. | 424/5 |
| 5,368,837 | 11/1994 | Baker et al. | 424/5 |
| 5,384,107 | 1/1995 | Singh et al. | 424/5 |

FOREIGN PATENT DOCUMENTS 498482   1/1992   European Pat. Off. .

OTHER PUBLICATIONS

CA 116:255269 (1992).
CA 82:138711 (1974).
CA 71:50424 (1969).

*Primary Examiner*—José G. Dees
*Assistant Examiner*—Barbara S. Frazier
*Attorney, Agent, or Firm*—Arthur H. Rosenstein

[57] ABSTRACT

Compounds having the structure

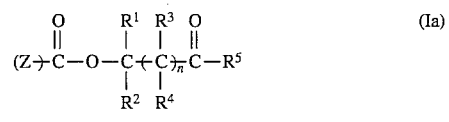

(Ia)

or

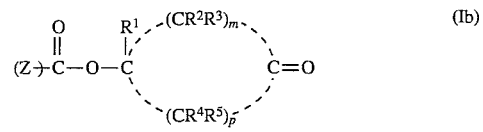

(Ib)

wherein (Z)COO is the residue of an iodinated aromatic acid;

n is an integer from 0 to 20;

$R^1$, $R^2$, $R^3$ and $R^4$ are independently H, alkyl, fluoroalkyl, cycloalkyl, aryl, aralkyl, alkoxy, aryloxy, halogen, hydroxy, acylamino, acetamidoalkyl, acetamidoaryl, —COO-alkyl, —COO-aryl, —COO-aralkyl, —CO-alkyl, —CO-aryl, —CO-heterocyclyl, cyano or heterocyclyl;

$R^5$ is H, alkyl, fluoroalkyl, cycloalkyl, aryl, aralkyl, alkoxyalkyl, heterocyclyl, or a Z-$CO_2$-$CR^1R^2$—$(CR^3R^4)_{\overline{n}}$ group, wherein Z, $R^1$, $R^2$, $R^3$, $R^4$ and n are as defined above, m is an integer from 0 to 10, p is an integer from 0 to 10, and m+p≧1 are useful as contrast agents in x-ray imaging compositions and methods.

8 Claims, No Drawings

IODINATED AROYLOXY KETONES

FIELD OF INVENTION

This invention relates to iodinated aroyloxy ketones which are particularly useful as contrast agents for x-ray imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson et al, *Pharmaceuticals in Medical Imaging*, 1990, MacMillan Publishing Company.

The following references describe various iodine containing compounds useful in preparing x-ray contrast compositions.

U.S. Pat. No. 3,097,228 describes derivatives of 2,4,6-triiodobenzoyloxyalkanoic acids having the structure

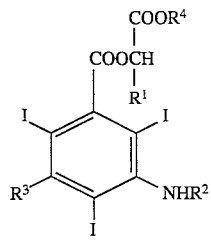

wherein $R^1$ is H or lower alkyl; $R^2$ is H or lower-alkanoyl; $R^3$ is H or lower alkanoylamino and $R^4$ is lower alkyl.

U.S. Pat. No. 3,144,479 describes iodinated benzoic acid esters having the formula

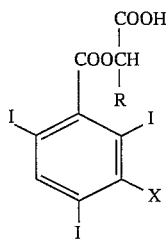

wherein X is an iodine atom or an amino group and R is selected from H, alkyl, alkoxyalkyl, i.e., $-(CH_2)_m-O-R''$, wherein R" is alkyl and m is 1 or 2, phenyl and a particular iodinated aromatic group.

However, these references do not disclose or suggest compounds featuring an ester group on an iodinated aromatic ring linked through an alkylene group to a ketone.

EP-A 498,482 describes nanoparticulate x-ray contrast compositions which have proven to be extremely useful in medical imaging. However, particulate contrast agents in certain in vivo applications can exhibit less than fully satisfactory stability, e.g., in plasma and blood.

Bacon et al, commonly-assigned U.S. patent application Ser. No. 07/990,987 filed Dec. 16, 1992, describe iodinated aroyloxy esters featuring a terminal —COOR group.

Bacon et al, commonly-assigned U.S. Pat. No. 5,260,478, describe various iodinated aroyloxy carboxamides. These compounds feature a terminal $-CO-RN^5R^6$ group.

It would be desirable to provide compounds for use as x-ray contrast agents having improved stability, e.g., in plasma and blood.

SUMMARY OF THE INVENTION

We have discovered and prepared novel iodinated aroyloxy ketones which are useful as contrast agents in x-ray imaging compositions and methods.

More specifically, in accordance with this invention, there are provided compounds having the structure

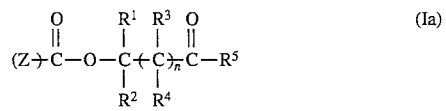  (Ia)

or

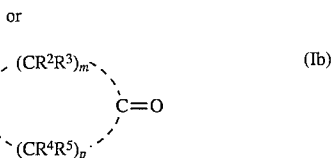  (Ib)

wherein (Z)COO is the residue of an iodinated aromatic acid;

n is an integer from 0 to 20;

$R^1$, $R^2$, $R^3$ and $R^4$ are independently H, alkyl, fluoroalkyl, cycloalkyl, aryl, aralkyl, alkoxy, aryloxy, halogen, hydroxy, acylamino, acetamidoalkyl, acetamidoaryl, —COO-alkyl, —COO-aryl, —COO-aralkyl, —CO-alkyl, —CO-aryl, —CO-heterocyclyl, cyano or heterocyclyl;

$R^5$ is H, alkyl, fluoroalkyl, cycloalkyl, aryl, aralkyl, alkoxyalkyl, heterocyclyl, or a

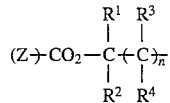

group, wherein Z $R^1$, $R^2$, $R^3$, $R^4$ and n are as defined above;

m is an integer from 0 to 10;

p is an integer from 0 to 10; and $m+p \geq 1$.

This invention further provides an x-ray contrast composition comprising the above-described compound and a method for medical x-ray diagnostic imaging which comprises administering to the body of a test subject an effective contrast producing amount of the above-described x-ray contrast composition.

It is an advantageous feature of this invention that novel compounds are provided which find particular utility as x-ray contrast agents.

It is another advantageous feature of this invention that compounds are provided having improved enzymatic stability and appropriate solubility profiles.

DESCRIPTION OF PREFERRED EMBODIMENTS

In structural formulae Ia and Ib above, (Z)COO is the residue of an iodinated aromatic acid. The iodinated aromatic acid can comprise one, two, three or more iodine atoms per molecule. Preferred species contain at least two, and more preferably, at least three iodine atoms per molecule. The iodinated compounds can contain substituents which do not deleteriously effect the contrast enhancing capability of the compound.

Illustrative examples of suitable aromatic acids include
diatrizoic acid,
metrizoic acid,
urokonic acid,
iothalamic acid,
triiodoisophthalic acid,
trimesic acid,
ioxaglic acid (hexabrix),
ioxitalamic acid,
tetraiodoterephthalic acid,
iodipamide, and the like.

In preferred embodiments, (Z-)COO is the residue of a substituted triiodobenzoic acid such as an acyl, carbamyl, and/or acylamino substituted triiodobenzoic acid. In a highly preferred embodiment, (Z-)COO is the residue of diatrizoic acid.

$R^1$, $R^2$, $R^3$ and $R^4$ independently represent H; linear or branched alkyl, preferably containing from 1 to 20, more preferably 1 to 8 carbon atoms such as methyl, ethyl, propyl, isopropyl, butyl, pentyl, hexyl and the like; fluoroalkyl, the alkyl portion of which is as described above and containing from 1 to (2m+1) fluorine atoms (where m=the number of carbon atoms in the alkyl group), such as trifluoromethyl; cycloalkyl, preferably containing from 3 to 8 carbon atoms such as cyclopropyl, cyclobutyl, cyclopentyl, cyclohexyl and adamantyl; aryl, preferably containing from 6 to 10 carbon atoms, such as phenyl and naphthyl; aralkyl, preferably containing from 7 to 12 carbon atoms, such as benzyl; alkoxy, the alkyl portion of which contains from 1 to 20 carbon atoms as described above; aryloxy, the aryl portion of which preferably contains from 6 to 10 carbon atoms as described above; halogen, such as fluorine, chlorine, bromine or iodine; hydroxy; acylamino, i.e., a

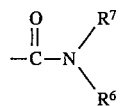

group; acetamidoalkyl, i.e.,

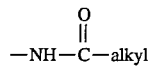

wherein alkyl is as defined above; acetamidoaryl, i.e.,

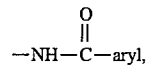

wherein aryl is as defined above; —COO-aryl, the aryl portion of which is as defined above; —COO-aralkyl, the aralkyl portion of which is as defined above; —COO-alkyl, the alkyl portion of which is as defined above; —CO-alkyl, the alkyl portion of which is as defined above; —CO-aryl, the aryl portion of which is as defined above; —CO-heterocyclyl, the heterocyclyl portion of which is as defined below; cyano; or heterocyclyl.

The heterocyclic aromatic radical can be monocyclic or bicyclic and preferably contains 5 to 12 ring atoms. The heterocyclyl radical preferably contains one or more S, N or O atoms as the heteroatoms. Examples of preferred heterocyclyl radicals include thienyl, furanyl, pyridinyl, pyrrolyl, quinolinyl, thiazolyl, imidazolyl, pyrimidinyl, pyrazinyl, pyrazolyl and the like.

$R^5$ represents H, alkyl as defined above; fluoroalkyl as defined above; cycloalkyl as defined for above; aryl as defined above; aralkyl as defined above; alkoxyalkyl, the alkyl and alkoxy portions of which are as defined above; a heterocyclyl aromatic radical as defined above; or a

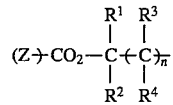

group, wherein Z, $R^1$, $R^2$, $R^3$, $R^4$ and n are as defined above.

$R^6$ and $R^7$ are independently a substituent as defined for $R^1$–$R^4$ above, or $R^6$ and $R^7$, taken together with the nitrogen atom to which they are attached, represent a 4–7 membered saturated or unsaturated nitrogen containing ring such as piperidyl, piperizinyl, pyrrolidinyl, and the like.

In structure Ib above, m and p preferably independently represent 0, 1, 2, 3, 4, 5, 6, 7, 8, 9 or 10. The sum of m+p must be greater than 1. In prefered embodiments

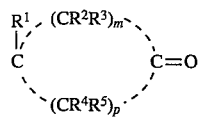

represents the atoms necessary to complete a carbocyclic, preferably saturated ring containing a ketone group such as cyclopropanone, cyclobutanone, cyclopentanone, cyclohexanone, cycloheptanone, cyclooctanone and the like, The alkyl, aryl, and heterocyclyl groups in structures Ia and Ib above can be unsubstituted or substituted with various substituents which do not adversely affect the stability or efficacy of the compounds as x-ray contrast agents such as alkyl, fluoroalkyl, cycloalkyl, aryl, aralkyl, alkoxy, aryloxy, hydroxy, acyloxy, halogen, such as fluorine, chlorine, bromine and iodine, acylamino, carboxy, carboalkoxy, carbamyl, carboxamido, cyano and the like. However, reactive substituents such as halogen are not preferred on the carbon atoms, if present in $R^5$ adjacent to the ketone group.

When contrast agents possessing high melting points are desired, e.g., when the agent is intended to be subjected to a wet grinding process as described below, it is particularly preferred that n=0, 1, 2, 3, or 4.

The compounds of this invention having the structures Ia and Ib above can be prepared respectively by contacting the carboxylate salt of an iodinated aromatic acid with a functionalized ketone having the formulae IIa or IIb

or

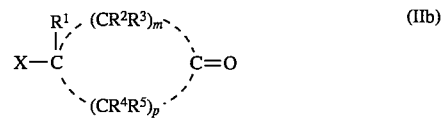

wherein X is a leaving group and n and $R^1$–$R^5$ are as defined above, in a suitable solvent. Suitable leaving groups include halogen, such as Br, I and Cl, sulfonyloxy, such as methanesulfonyloxy and toluenesulfonyloxy. The carboxylate salts of iodinated aromatic acids and the functionalized ketones useful as the starting materials in the preparation of the compounds of this invention are known compounds and/or can be prepared by techniques known in the art. For example, suitable ketones include commercially available bromoketones and chloroketones derivatives as exemplified below. General reaction schemes are as follows:

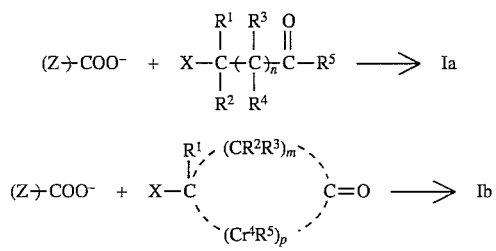

The reaction can take place at various temperatures ranging between −78° C. and 100° C., and preferably between −40° C. and 50° C. For convenience, the reaction can take place at ambient pressure, however, higher and lower pressures are contemptated.

The reaction can take place in any suitable solvent. Suitable solvents include N,N-dimethylformamide (DMF).

The following are specific illustrative examples of preferred compounds of this invention that have been prepared:

2-Oxo-2-phenylethyl 3,5-bis(acetylamino)-2,4,6-triiodobenzoate (WIN 69669);

1-Methyl-2-oxo-2-phenylethyl 3,5-bis (acetylamino)-2,4,6-triiodobenzoate (WIN 69693);

2-(4-Methoxyphenyl)-2-oxoethyl 3,5-bis (acetylamino)-2,4,6-triiodobenzoate (WIN 69839);

2-(4-Methylphenyl)-2-oxoethyl 3,5-bis (acetylamino)-2,4,6-triiodobenzoate (WIN 71424)

2-Oxopropyl 3,5-bis(acetylamino)-2,4,6-triiodobenzoate (WIN 69662);

3-(1,1-Dimethyl)-2-oxopropyl 3,5-bis(acetylamino)- 2,4,6-triiodobenzoate (WIN 69940);

2-(1-Adamantyl)-2-oxoethyl 3,5-bis(acetylamino)- 2,4,6-triiodobenzoate (WIN 71200);

2-[3-(3-Methyl-2-oxo)furanyl]-2-oxoethyl 3,5-bis(acetylamino)- 2,4,6-triiodobenzoate (WIN 68681);

2-Oxo-1,3-propyl bis [3,5-bis(acetylamino) -2,4,6-triiodobenzoate] (WIN 69661);

1-Oxo-2-cyclopentyl 3,5-bis(acetylamino)-2,4,6-triiodobenzoate (WIN 71627).

3-(2,4-Dioxopentyl) 3,5-bis(acetylamino)-2,4,6-triiodobenzoate (WIN 69834); and

1-Ethoxy-1,3-dioxo-2-butyl 3,5-bis(acetylamino)- 2,4,6-triiodobenzoate (WIN 70697).

Preferred compounds conform to structure Ia above, wherein Z—(COO) is the residue of diatrizoic acid and n=0 as set forth below:

| (WIN) | COMPOUND | $R^1$ | $R^2$ | $R^5$ | m.p. °C. |
|---|---|---|---|---|---|
| 69662 | 1 | H | H | —$CH_3$ | >250 dec. |
| 69940 | 2 | H | H | —$C(CH_3)_3$ | 280 dec. |
| 71200 | 3 | H | H | -adamantyl | 260 dec. |
| 68681 | 4 | H | H | (3-methyl-2-oxo-furanyl group) | 243–4 dec. |
| 69661 | 5 | H | H | —$CH_2O_2C$—(3,5-bis(NHAc)-2,4,6-triiodophenyl) | >270 dec. |
| 69669 | 6 | H | H | —$C_6H_5$ | >260 dec. |
| 69693 | 7 | H | $CH_3$ | —$C_6H_5$ | 138–139 |
| 69839 | 8 | H | H | —$C_6H_4(4\text{-}OCH_3)$ | 258–260 dec. |
| 71424 | 9 | H | H | —$C_6H_4(4\text{-}CH_3)$ | 267 dec. |
| 69834 | 10 | H | $COCH_3$ | —$CH_3$ | 240–243 dec. |
| 70697 | 11 | H | $CO_2C_2H_5$ | —$CH_3$ | 248 dec. |

Another preferred compound conforming to structure Ib above, wherein (Z)—COO is the residue of diatrizoic acid, n=3, $R^1$–$R^3$=H and p=0 is WIN 71627 (m.p. 236–238 dec.).

When used as an x-ray contrast agent, the compound of this invention preferably comprises at least about 35%, more preferably 40% iodine by weight.

In preferred embodiments, the compounds of this invention can be formulated into particulate x-ray contrast compositions, preferably nanoparticulate x-ray contrast compositions, as described in commonly-owned EPO 498,482, the disclosure of which is hereby incorporated by reference in its entirety. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition. Preferred surface modifiers include nonionic surfactants. The nanoparticulate compositions can include a cloud point modifier to reduce particle aggregation during heat sterilization.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–25% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 50 to 350 mg of iodine per kilogram of body weight of the subject for many imaging applications. For some applications, e.g., lymphography, lower doses, e.g., 0.5–20 mg I/kg, can be effective.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a convention manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intramuscular administration, intralesional administration, intrathecal administration, intracisternal administration, oral administration, administration via inhalation, administration directly into a body cavity, e.g., arthrography, and the like.

In addition to preferred applications, i.e., for blood pool, liver, spleen and lymph node imaging, the x-ray contrast compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1

Preparation of WIN 69662

To a stirred mixture of sodium diatrizoate (63.6 g, 0.1 mol) and 250 ml of N,N-dimethylformamide (DMF) was added chloroacetone (10 ml, 0.12 mol). The resulting mixture was stirred at room temperature overnight and concentrated on a rotary evaporator. The resulting white residue was slurried in distilled water (300 ml), collected, washed with water and ethanol successively and dried in the vacuum oven at 80°–85° C. to afford 66.8 g (100%) of a white powder: mp dec. >250° C.; MS(FAB): 671 (MH+). The $^1$H-NMR(300 MHz) was consistent with the desired structure. Calculated for $C_{14}H_{13}I_3N_2O_5$: C, 25.10; H, 1.96; N, 4.18; I, 56.82. Found: C, 25.24; H, 1.86; N, 4.16; I, 56.61.

EXAMPLE 2

Preparation of WIN 69669

To a stirred mixture of sodium diatrizoate (63.6 g, 0.1 tool) and DMF (250 ml) was added phenacyl chloride (16 ml, 0.12 tool). The resulting mixture was stirred at room temperature overnight and concentrated on a rotary evaporator. The residue was slurried in distilled water (300 ml). The white product was collected, washed with water and ethanol successively, dried in the vacuum oven at 80°–85° C. to afford 69.4 g (95%) of a white crystalline solid: mp dec. >260° C.; MS (FAB): 733 (MH+). The $^1$H-NMR (300 MHz) was consistent with the structure. Calculated for $C_{19}H_{15}I_3N_2O_5$: C, 31.17; H, 2.07; N, 3.83; I, 52.01. Found: C, 31.30; H, 1.93; N, 3.75; I, 51.82.

EXAMPLE 3

Preparation of WIN 71627

In a manner similar to the procedures described in Examples 1 and 2 above, WIN 71627 was prepared from sodium diatrizoate and bromocyclopentanone. The MS and spectral data (300 MHz) were consistent with the desired structure.

EXAMPLES 4–12

In a manner similar to the procedures described in Examples 1 and 2 above, the other compounds set forth in the Table above were prepared. In each case, the MS and spectral date (300 MHz) were consistent with the desired product.

EXAMPLE 13

Imaging with WIN 69669

A formulation was prepared by wet grinding an aqueous dispersion of WIN 69669 prepared as described in Example 2 above. The aqueous dispersion comprised 15% (w/v) WIN 69669 and 4% (w/v)F108. F108 is a block copolymer of ethylene oxide and propylene oxide commercially available from BASF Corp. as Pluronic™ F108. The final particle size was 225 nm. The formulation was dosed at 3 ml/kg and injected intravenously into the ear vein of a rabbit. At 5 minutes, 15 minutes, 30 minutes, 60 minutes and 120 minutes post-injection, the rabbit was subjected to a conventional computed tomography (CT) x-ray imaging procedure using a Toshiba 900S imager. The studies were carried out at the Center for Imaging and Pharmaceutical Research, Massachusetts General Hospital, Boston, Mass. The formulations provided images demonstrating good contrast enhancement of the blood pool and excellent contrast enhancement of the liver/spleen. No acute or chronic safety problems were noted in the rabbit as a result of the injection of the formulation.

The invention has been described in detail with particular reference to certain preferred embodiments thereof, but it will be understood that variations and modifications can be effected within the spirit and scope of the invention.

We claim:

1. A compound having the structure

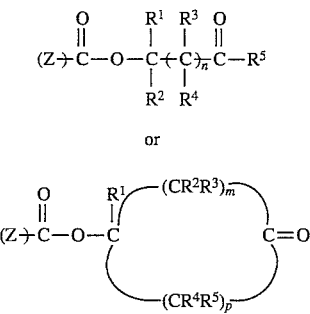

wherein $(Z)\text{-COO}$ is the residue of a triiodinated aromatic acid;

n is an integer from 0 to 20;

$R^1$, $R^2$, $R^3$ and $R^4$ are independently H, alkyl, fluoroalkyl, cycloalkyl, aryl, aralkyl, alkoxy, aryloxy, halogen, hydroxy, acylamino, acetamidoalkyl, acetamidoaryl, —COO-alkyl, —COO-aryl, —COO-aralkyl, —CO-alkyl, —CO-aryl, or cyano;

$R^5$ is H, alkyl, fluoroalkyl, cycloalkyl, aryl,

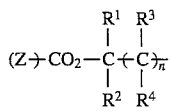

aralkyl, alkoxyalkyl, or a group, wherein Z, $R^1$, $R^2$, $R^3$, $R^4$ and n are as defined above;

m is an integer from 0 to 10;

p is an integer from 0 to 10; and m+p>1.

2. The compound of claim 1 wherein $(Z)\text{-COO}$ is the residue of diatrizoic acid.

3. The compound of claim 1 wherein n is 0, 1, 2, 3 or 4.

4. The compound of claim 1 wherein n=0 and $R^1$ and $R^2$=H.

5. The compound of claim 1, selected from the group consisting of:

2-Oxo-2-phenylethyl 3,5-bis(acetylamino)-2,4,6-triiodobenzoate (WIN 69669);

1-Methyl-2-oxo-2-phenylethyl 3,5-bis(acetylamino)-2,4,6-triiodobenzoate (WIN 69693);

2-(4-Methoxyphenyl)-2-oxoethyl 3,5-bis(acetylamino)-2,4,6-triiodobenzoate (WIN 69839);

2-(4-Methylphenyl)-2-oxoethyl 3,5-bis(acetylamino)-2,4,6-triiodobenzoate (WIN 71424);

2-Oxopropyl 3,5-bis(acetylamino)-2,4,6-triiodobenzoate (WIN 69662);

3-(1,1-Dimethyl)-2-oxopropyl 3,5-bis(acetylamino)-2,4,6-triiodobenzoate (WIN 69940);

2-(1-Adamantyl)-2-oxoethyl 3,5-bis(acetylamino)-2,4,6-triiodobenzoate (WIN 71200);

2-Oxo-1,3-propyl bis [3,5-bis (acetylamino)-2,4,6-triiodobenzoate] (WIN 69661);

1-Oxo-2-cyclopentyl 3,5-bis(acetylamino)-2,4,6-triiodobenzoate (WIN 71627).

3-(2,4-Dioxopentyl) 3,5-bis (acetylamino)-2,4,6-triiodobenzoate (WIN 69834); and 1-Ethoxy-1,3-dioxo-2-butyl 3,5-bis(acetylamino)-2,4,6-triiodobenzoate (WIN 70697).

6. An x-ray contrast composition comprising the compound of claim 1.

7. The x-ray contrast composition of claim 6 further including a pharmaceutically acceptable carrier.

8. A method for medical x-ray diagnostic imaging which comprises administering to the body of a mammal a contrast effective amount of the x-ray contrast composition of claim 6.

* * * * *